United States Patent [19]
Hamilton et al.

[11] Patent Number: 5,874,449
[45] Date of Patent: Feb. 23, 1999

[54] N-LINKED SULFONAMIDES OF HETEROCYCLIC THIOESTERS

[75] Inventors: Gregory S. Hamilton, Catonsville; Jia-He Li, Cockeysville; Wei Huang, Baltimore, all of Md.

[73] Assignee: GPI NIL Holdings, Inc., Wilmington, Del.

[21] Appl. No.: 775,584

[22] Filed: Dec. 31, 1996

[51] Int. Cl.$^6$ ............ A61K 31/40; A61K 31/445; C07D 207/48; C07D 211/96

[52] U.S. Cl. ............ 514/330; 514/423; 514/424; 546/192; 546/245; 548/530; 548/542

[58] Field of Search ............ 514/709, 277, 514/359, 330, 423, 424; 558/230, 250; 546/112, 192, 245; 548/530, 542

[56] References Cited

U.S. PATENT DOCUMENTS

| | | | |
|---|---|---|---|
| 4,070,361 | 1/1978 | Petrillo | 260/293.85 |
| 5,192,773 | 3/1993 | Armistead et al. | 514/315 |
| 5,536,723 | 7/1996 | Loscalzo et al. | 514/247 |
| 5,585,397 | 12/1996 | Tung et al. | 514/473 |

FOREIGN PATENT DOCUMENTS

| | | |
|---|---|---|
| WO 94/05639 | 3/1994 | WIPO . |
| WO 95/24385 | 9/1995 | WIPO . |
| WO 96/33184 | 10/1996 | WIPO . |
| WO 96/33187 | 10/1996 | WIPO . |
| WO 96/41609 | 12/1996 | WIPO . |
| WO 97/36869 | 10/1997 | WIPO . |

OTHER PUBLICATIONS

Holt, Dennis A. et al., "Structure–Activity Studies of Synthetic FKBP Ligands as Peptidyl–Prolyl Isomerase Inhibitors," Biorg. Med. Chem. Lett., 1994, 4(2) 315–320.

Holt, Dennis A. et al., "Design Synthesis, and Kinetic Evaluation of High–Affinity FKBP Ligands and the X–ray Crystal Structures of Their Complexes with FKBP12," J. Am. Chem. Soc., 1993, 115, 9925–9938.

*Primary Examiner*—Johann Richter
*Assistant Examiner*—Jane C. Osweckí
*Attorney, Agent, or Firm*—Gary M. Nath; Todd L. Juneau; Nath & Associates

[57] ABSTRACT

This invention relates to neurotrophic low molecular weight, small molecule N-linked sulfonamides of heterocyclic thioesters having an affinity for FKBP-type immunophilins, and their use as inhibitors of the enzyme activity associated with immunophilin proteins, particularly peptidyl-prolyl isomerase, or rotamase, enzyme activity.

33 Claims, No Drawings

N-LINKED SULFONAMIDES OF HETEROCYCLIC THIOESTERS

BACKGROUND OF THE INVENTION

1. Field of Invention

This invention relates to neurotrophic low molecular weight, small molecule N-linked sulfonamides of heterocyclic thioesters having an affinity for FKBP-type immunophilins, and their use as inhibitors of the enzyme activity associated with immunophilin proteins, particularly peptidyl-prolyl isomerase, or rotamase, enzyme activity.

2. Description of Related Art

The term immunophilin refers to a number of proteins that serve as receptors for the principal immunosuppressant drugs, cyclosporin A (CsA), FK506 and rapamycin. Known classes of immunophilins are cyclophilins and FK506 binding proteins, or FKBPs. Cyclosporin A binds to cyclophilin A while FK506 and rapamycin bind to FKBP12. These immunophilin-drug complexes interface with various intracellular signal transduction systems, especially the immune and nervous systems.

Immunophilins are known to have peptidyl-prolyl isomerase (PPIase), or rotamase, enzyme activity. It has been determined that rotamase enzyme activity plays a role in the catalyzation of the interconversion of the cis and trans isomers of peptide and protein substrates for the immunophilin proteins.

Immunophilins were originally discovered and studied in the immune tissue. It was initially postulated by those skilled in the art that inhibition of the immunophilins' rotamase activity leads to inhibition of T-cell proliferation, thereby causing the immunosuppressive activity exhibited by immunosuppressant drugs, such as cyclosporin A, FK506 and rapamycin. Further study has shown that the inhibition of rotamase activity, in and of itself, does not result in immunosuppressive activity. Schreiber et al., *Science*, 1990, vol. 250, pp. 556–559. Instead, immunosuppression appears to stem from the formulation of a complex of immunosuppressant drugs and immunophilins. It has been shown that the immunophilin-drug complexes interact with ternary protein targets as their mode of action. Schreiber et al., *Cell*, 1991, vol. 66, pp. 807–815. In the case of FKBP-FK506 and cyclophilin-CsA, the immunophilin-drug complexes bind to the enzyme calcineurin and inhibit the T-cell receptor signalling which leads to T-cell proliferation. Similarly, the immunophilin-drug complex of FKBP-rapamycin interacts with the RAFT1/FRAP protein and inhibits the IL-2 receptor signalling.

Immunophilins have been found to be present at high concentrations in the central nervous system. Immunophilins are enriched 10–50 times more in the central nervous system than in the immune system. Within neural tissues, immunophilins appear to influence nitric oxide synthesis, neurotransmitter release and neuronal process extension.

It has been found that picomolar concentrations of an immunosuppressant such as FK506 and rapamycin stimulate neurite outgrowth in PC12 cells and sensory neurons, namely dorsal root ganglion cells (DRGs). Lyons et al., *Proc. of Natl. Acad. Sci.*, 1994, vol. 91, pp. 3191–3195. In whole animal experiments, FK506 has been shown to stimulate nerve regeneration following facial nerve injury.

Surprisingly, it has been found that certain compounds with a high affinity for FKBPs are potent rotamase inhibitors and exhibit excellent neurotrophic effects. Furthermore, these rotamase inhibitors are devoid of immunosuppressive activity. These findings suggest the use of rotamase inhibitors in treating various peripheral neuropathies and enhancing neuronal regrowth in the central nervous system (CNS). Studies have demonstrated that neurodegenerative disorders such as Alzheimer's disease, Parkinson's disease, and amyotrophic lateral sclerosis (ALS) may occur due to the loss, or decreased availability, of a neurotrophic substance specific for a particular population of neurons affected in the disorder.

Several neurotrophic factors affecting specific neuronal populations in the central nervous system have been identified. For example, it has been hypothesized that Alzheimer's disease results from a decrease or loss of nerve growth factor (NGF). It has thus been proposed to treat Senile Dementia Alzheimer's Type (SDAT) patients with exogenous nerve growth factor or other neurotrophic proteins, such as brain derived growth factor, glial derived growth factor, ciliary neurotrophic factor and neurotropin-3, to increase the survival of degenerating neuronal populations.

Clinical application of these proteins in various neurological disease states is hampered by difficulties in the delivery and bioavailability of large proteins to nervous system targets. By contrast, immunosuppressant drugs with neurotrophic activity are relatively small and display excellent bioavailability and specificity. However, when administered chronically, immunosuppressant drugs exhibit a number of potentially serious side effects including nephrotoxicity, such as impairment of glomerular filtration and irreversible interstitial fibrosis (Kopp et al., *J. Am. Soc. Nephrol.*, 1991, 1:162); neurological deficits, such as involuntary tremors, or non-specific cerebral angina, such as non-localized headaches (De Groen et al., *N. Engl. J. Med.*, 1987, 317:861); and vascular hypertension with complications resulting therefrom (Kahan et al., *N. Engl. J. Med.*, 1989, 321:1725).

In order to prevent the side effects associated with use of the immunosuppressant compounds, the present invention provides non-immunosuppressive compounds containing small molecule FKBP rotamase inhibitors for enhancing neurite outgrowth, and promoting neuronal growth and regeneration in various neuropathological situations where neuronal repair can be facilitated, including: peripheral nerve damage caused by physical injury or disease state such as diabetes; physical damage to the central nervous system (spinal cord and brain); brain damage associated with stroke; and neurological disorders relating to neurodegeneration, such as Parkinson's disease, SDAT (Alzheimer's disease), and amyotrophic lateral sclerosis.

SUMMARY OF THE INVENTION

The present invention relates to neurotrophic low molecular weight, small molecule compounds having an affinity for FKBP-type immunophilins. Once bound to these proteins, the neurotrophic compounds are potent inhibitors of the enzyme activity associated with immunophilin proteins, particularly peptidyl-prolyl isomerase, or rotamase, enzyme activity. A key feature of the compounds of the present invention is that they do not exert any significant immunosuppressive activity in addition to their neurotrophic activity. Another significant feature is the novel addition of a thioester linkage and an unexpected increase in bioavailability and potency as compared to compounds lacking a thioester linkage.

Specifically, the present invention relates to a compound of formula I:

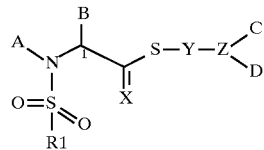

or a pharmaceutically acceptable salt thereof, wherein:

A and B are taken together, with the nitrogen and carbon atoms to which they are respectively attached, to form a 5–7 membered saturated or unsaturated heterocyclic ring containing any combination of $CH_2$, O, S, SO, $SO_2$, NH or $NR_2$ in any chemically stable oxidation state;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide; and $R_1$ is selected from the group consisting of Ar, or $C_3$–$C_8$ cycloalkyl, or $C_1$–$C_6$ straight or branched chain alkyl or alkenyl, or $C_1$–$C_6$ straight or branched chain alkyl or alkenyl which is substituted in one or more positions with Ar or $C_3$–$C_8$ cycloalkyl.

In preferred embodiments, Ar is selected from the group consisting of naphthyl, indolyl, furyl, thiazolyl, thienyl, pyridyl, and phenyl.

A preferred embodiment of this invention is a compound of formula II:

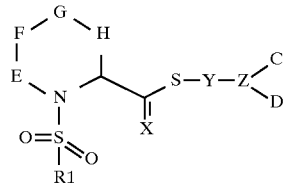

or a pharmaceutically acceptable salt thereof, wherein:

E, F, G and H are independently $CH_2$, O, S, SO, $SO_2$, NH or $NR_2$;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide; and $R_1$ is selected from the group consisting of Ar, or $C_3$–$C_8$ cycloalkyl, or $C_1$–$C_6$ straight or branched chain alkyl or alkenyl, or $C_1$–$C_6$ straight or branched chain alkyl or alkenyl which is substituted in one or more positions with Ar or $C_3$–$C_8$ cycloalkyl.

In preferred embodiments, Ar is selected from the group consisting of naphthyl, indolyl, furyl, thiazolyl, thienyl, pyridyl, and phenyl.

Another preferred embodiment is a compound of formula III:

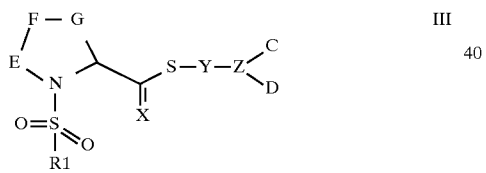

or a pharmaceutically acceptable salt thereof, wherein:

E, F, G and H are independently $CH_2$, O, S, SO, $SO_2$, NH or $NR_2$;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:

hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$,) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide; and $R_1$ is selected from the group consisting of Ar, or $C_3$–$C_8$ cycloalkyl, or $C_1$–$C_6$ straight or branched chain alkyl or alkenyl, or $C_1$–$C_6$ straight or branched chain alkyl or alkenyl which is substituted in one or more positions with Ar or $C_3$–$C_8$ cycloalkyl.

In preferred embodiments, Ar is selected from the group consisting of naphthyl, indolyl, furyl, thiazolyl, thienyl, pyridyl, and phenyl.

A further particularly preferred embodiment of this invention is a compound of formula IV:

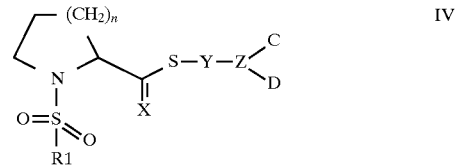

or a pharmaceutically acceptable salt thereof, wherein:

n is 1, 2 or 3 forming a 5–7 member heterocyclic ring;

X is either O or S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$) bridging alkyl wherein a bridge is formed between the nitrogen and a carbon atom of said alkyl or alkenyl chain containing said heteroatom to form a ring, wherein said ring is optionally fused to an Ar group;

C and D are independently:
hydrogen, or Ar, or $C_1$–$C_6$ straight or branched chain alkyl or alkenyl, which is optionally substituted in one or more position(s) with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, and ($C_1$–$C_4$,) bridging alkyl wherein a bridge is formed between the nitrogen and a carbon atom of said alkyl or alkenyl chain containing said heteroatom to form a ring, wherein said ring is optionally fused to an Ar group;

wherein Ar is a mono-, bi- or tricyclic, carbo- or heterocyclic ring, wherein the ring is either unsubstituted or substituted in one to three position(s) with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; wherein the individual ring sizes are 5–6 members; wherein the heterocyclic ring contains 1–6 heteroatom(s) selected from the group consisting of O, N, S, and a combination thereof; wherein aromatic or tertiary alkyl amines are optionally oxidized to a corresponding N-oxide; and $R_1$ is selected from the group consisting of Ar, or $C_3$–$C_8$ cycloalkyl, or $C_1$–$C_6$ straight or branched chain alkyl or alkenyl, or $C_1$–$C_6$ straight or branched chain alkyl or alkenyl which is substituted in one or more positions with Ar or $C_3$–$C_8$ cycloalkyl.

In preferred embodiments, Ar is selected from the group consisting of naphthyl, indolyl, furyl, thiazolyl, thienyl, pyridyl, and phenyl.

The present invention also relates to a pharmaceutical composition comprising a neurotrophically effective amount of the compound of formula I, II, III or IV, and a pharmaceutically acceptable carrier.

The present invention further relates to a method of effecting a neuronal activity in an animal, comprising:
administering to the animal a neurotrophically effective amount of the compound of formula I, II, III or IV.

DETAILED DESCRIPTION OF THE INVENTION

Definitions

"Alkyl" means a branched or unbranched saturated hydrocarbon chain containing 1 to 6 carbon atoms, such as methyl, ethyl, propyl, iso-propyl, butyl, iso-butyl, tert-butyl, n-pentyl, n-hexyl, and the like, unless otherwise indicated.

"Alkoxyl" means the group -OR wherein R is alkyl as herein defined. Preferably, R is a branched or unbranched saturated hydrocarbon chain containing 1 to 3 carbon atoms.

"Halo" means fluoro, chloro, bromo, or iodo, unless otherwise indicated.

"Phenyl" includes all possible isomeric phenyl radicals, optionally monosubstituted or multi-substituted with substituents selected from the group consisting of alkyl, alkoxy, hydroxy, halo, and haloalkyl.

The term "pharmaceutically acceptable salt" refers to salts of the subject compounds which posses the desired pharmacological activity and which are neither biologically nor otherwise undesirable. The salts can be formed with inorganic acids such as acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate heptanoate, hexanoate, hydrochloride hydrobromide, hydroiodide, 2-hydroxyethanesulfonate, lactate, maleate, methanesulfonate, 2-naphthalenesulfonate, nicotinate, oxalate, thiocyanate, tosylate and undecanoate. Base salts include ammonium salts, alkali metal salts such as sodium and potassium salts, alkaline earth metal salts such as calcium and magnesium salts, salt with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides; dialkyl sulfates like dimethyl, diethyl, dibutyl and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The compounds of this invention possess at least one asymmetric center and thus can be produced as mixtures of stereoisomers or as individual enantiomers or diastereomers. The individual stereoisomers may be obtained by using an optically active starting material, by resolving a racemic or non-racemic mixture of an intermediate at some appropriate stage of the synthesis, or by resolution of the compound of formula (I). It is understood that the individual stereoisomers as well as mixtures (racemic and non-racemic) of stereoisomers are encompassed by the scope of the present invention. The S-stereoisomer at atom 1 of formula I is most preferred due to its greater activity.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other.

"Diastereoisomers" are stereoisomers which are not mirror images of each other.

"Racemic mixture" means a mixture containing equal parts of individual enantiomers. "Non-racemic mixture" is a mixture containing unequal parts of individual enantiomers or stereoisomers.

The term "treatment" as used herein covers any treatment of a disease and/or condition in an animal, particularly a human, and includes:

(i) preventing a disease and/or condition from occurring in a subject which may be predisposed to the disease and/or condition but has not yet been diagnosed as having it;

(ii) inhibiting the disease and/or condition, i.e., arresting its development; or (iii) relieving the disease and/or condition, i.e., causing regression of the disease and/or condition.

The system used in naming the compounds of the present invention is shown below, using a compound of formula IV as an example.

A compound of the present invention, especially Formula 4, wherein n is 1, X is O, Y is $(CH_2)_2$, Z is $CH_2$, C is p-Methoxyphenyl, D is H and $R_1$ is Phenyl, is named 3-(para-Methoxyphenyl)-1-propylmercaptyl(2s)-N-(benzenesulfonyl)pyrrolidine-2-carboxylate.

Compounds of the Invention

The neurotrophic low molecular weight, small molecule FKBP inhibitor compounds of this invention have an affinity for FKBP-type immunophilins, such as FKBP12. When the neurotrophic compounds of this invention are bound to an FKBP-type immunophilin, they have been found to inhibit the prolyl-peptidyl cis-trans isomerase activity, or rotamase, activity of the binding protein and unexpectedly stimulate neurite growth.

Specific exemplifications of these embodiments are presented in TABLE I.

TABLE I

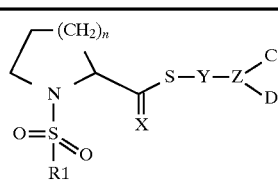

| No. | n | Y | Z | C | D | R1 |
|---|---|---|---|---|---|---|
| 1 | 1 | $CH_2$ | CH | Phenyl | H | Phenyl |
| 2 | 1 | $CH_2$ | CH | Phenyl | H | α-Methylphenyl |
| 3 | 1 | $CH_2$ | CH | Phenyl | H | 4-Methylphenyl |
| 4 | 1 | $(CH_2)_2$ | CH | p-Methoxyphenyl | H | Phenyl |
| 5 | 1 | $(CH_2)_2$ | CH | p-Methoxyphenyl | H | α-Methylphenyl |
| 6 | 1 | $(CH_2)_2$ | CH | p-Methoxyphenyl | H | 4-Methylphenyl |
| 7 | 1 | $(CH_2)_2$ | CH | Phenyl | Phenyl | Phenyl |
| 8 | 1 | $(CH_2)_2$ | CH | Phenyl | Phenyl | α-Methylphenyl |
| 9 | 1 | $(CH_2)_2$ | CH | Phenyl | Phenyl | 4-Methylphenyl |
| 10 | 2 | $(CH_2)_3$ | CH | Phenyl | H | Phenyl |
| 11 | 2 | $(CH_2)_3$ | CH | Phenyl | H | α-Methylphenyl |
| 12 | 2 | $(CH_2)_3$ | CH | Phenyl | H | 4-Methylphenyl |

TABLE I-continued

| No. | n | Y | Z | C | D | R1 |
|---|---|---|---|---|---|---|
| 13 | 2 | $(CH_2)_3$ | CH | Phenyl | H | 3, 4, 5-trimethoxyphenyl |
| 14 | 2 | $(CH_2)_3$ | CH | Phenyl | H | Cyclohexyl |
| 15 | 2 | Direct | CH | 3-Phenylpropyl | 3-Phenylpropyl | Phenyl |
| 16 | 2 | Direct | CH | 3-Phenylpropyl | 3-Phenylpropyl | α-Methylphenyl |
| 17 | 2 | Direct | CH | 3-Phenylpropyl | 3-Phenylpropyl | 4-Methylphenyl |
| 18 | 2 | Direct | CH | 3-Phenylethyl | 3-Phenylethyl | 4-Methylphenyl |
| 19 | 2 | Direct | CH | 3-(4-Methoxyphenyl)propyl | 3-Phenylpropyl | 4-Methylphenyl |
| 20 | 2 | Direct | CH | 3-(2-Pyridyl)propyl | 3-Phenylpropyl | 4-Methylphenyl |

The most preferred compounds of formula IV are:

3-(para-Methoxyphenyl)-1-propylmercaptyl(2S)-N-(benzenesulfonyl)pyrrolidine-2-carboxylate(4);

3-(para-Methoxyphenyl)-1-propylmercaptyl(2S)-N-(α-toluenesulfonyl)pyrrolidine-2-carboxylate (5);

3-(para-Methoxyphenyl)-1-propylmercaptyl(2S)-N-(α-toluenesulfonyl)pyrrolidine-2-carboxylate (6); and 1.5-Diphenyl-3-pentylmercaptyl N-(para-toluenesulfonyl)pipecolate (18).

The compounds of the present invention exist as stereoisomeric forms, either enantiomers or diastereoisomers. Included within the scope of the invention are the enantiomers, the racemic form, and diastereoisomeric mixtures. Enantiomers and diastereoisomers can be separated by methods known to those skilled in the art.

Methods of Using the Compounds of the Invention

The compounds of the present invention have an affinity for the FK506 binding protein, particularly FKBP12, which is present in the neuronal tissue. When the inventive compounds bind to FKBP in neuronal tissue, they exhibit excellent neurotrophic activity. This activity is useful in the stimulation of damaged neurons, the promotion of neuronal regeneration, the prevention of neurodegeneration, and the treatment of several neurological disorders known to be associated with neuronal degeneration and peripheral neuropathies.

For the foregoing reasons, the present invention further relates to a method of effecting a neuronal activity in an animal, comprising:

administering to the animal a neurotrophically effective amount of a compound of formula I, II, III or IV.

In a preferred embodiment, the neuronal activity is selected from the group consisting of stimulation of damaged neurons, promotion of neuronal regeneration, prevention of neurodegeneration and treatment of neurological disorder.

The neurological disorders that may be treated include but are not limited to: trigeminal neuralgia; glossopharyngeal neuralgia; Bell's Palsy; myasthenia gravis; muscular dystrophy; amyotrophic lateral sclerosis; progressive muscular atrophy; progressive bulbar inherited muscular atrophy; herniated; ruptured or prolapsed invertabrae disk syndromes; cervical spondylosis; plexus disorders; thoracic outlet destruction syndromes; peripheral neuropathic such as those caused by lead, dapsone, ticks, porphyria, or Guillain-Barré syndrome; Alzheimer's disease; and Parkinson's disease.

The compounds of the present invention are particularly useful for treating a neurological disorder selected from the group consisting of: peripheral neuropathy caused by physical injury or disease state, physical damage to the brain, physical damage to the spinal cord, stroke associated with brain damage, and neurological disorder relating to neurodegeneration. Examples of neurological disorders relating to neurodegeneration are Alzheimer's Disease, Parkinson's Disease, and amyotrophic lateral sclerosis.

For these purposes the compounds of the present invention may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneally, intrathecally, intraventricularly, intrasternal and intracranial injection or infusion techniques.

To be effective therapeutically as central nervous system targets, the compounds of the present invention should readily penetrate the blood-brain barrier when peripherally administered. Compounds which cannot penetrate the blood-brain barrier can be effectively administered by an intraventricular route or other appropriate delivery system suitable for adminstration to the brain.

The compounds of the present invention may be administered in the form of sterile injectable preparations, for example, as sterile injectable aqueous or oleaginous suspensions. These suspensions may be formulated according to techniques known in the art using suitable dispersing or wetting agents and suspending agents. The sterile injectable preparations may also be sterile injectable solutions or suspensions in non-toxic parenterally-acceptable diluents or solvents, for example, as solutions in 1,3-butanediol. Among the acceptable vehicles and solvents that may be employed are water, Ringer's solution and isotonic sodium chloride solution. In addition, sterile, fixed oils are conventionally employed as solvents or suspending mediums. For this purpose, any bland fixed oil may be employed including synthetic mono- or di-glycerides. Fatty acids such as oleic acid and its glyceride derivatives, including olive oil and castor oil, especially in their polyoxyethylated versions, are useful in the preparation of injectables. These oil solutions or suspensions may also contain long-chain alcohol diluents or dispersants.

The compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds of this invention may also be administered rectally in the form of suppositories. These compositions can be prepared by mixing the drug with a suitable non-irritating excipient which is solid at room temperature, but liquid at rectal temperature and, therefore, will melt in the rectum to release the drug. Such materials include cocoa butter, beeswax and polyethylene glycols.

The compounds of this invention may also be administered topically, especially when the conditions addressed for treatment involve areas or organs readily accessible by topical application, including neurological disorders of the eye, the skin, or the lower intestinal tract. Suitable topical formulations are readily prepared for each of these areas.

For topical application to the eye, or ophthalmic use, the compounds can be formulated as micronized suspensions in isotonic, pH adjusted sterile saline, or, preferably, as solutions in isotonic, pH adjusted sterile saline, either with or without a preservative such as benzylalkonium chloride. Alternatively for the ophthalmic uses the compounds may be formulated in an ointment such as petrolatum.

For topical application to the skin, the compounds can be formulated in a suitable ointment containing the compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, the compounds can be formulated in a suitable lotion or cream containing the active compound suspended or dissolved in, for example, a mixture of one or more of the following: mineral oil, sorbitan monostearate, polysorbate 60, cetyl esters wax, cetearyl alcohol, 2-octyldodecanol, benzyl alcohol and water.

Topical application for the lower intestinal tract an be effected in a rectal suppository formulation (see above) or in a suitable enema formulation.

Dosage levels on the order of about 0.1 mg to about 10,000 mg of the active ingredient compound are useful in the treatment of the above conditions, with preferred levels of about 0.1 mg to about 1,000 mg. The amount of active ingredient that may be combined with the carrier materials to produce a single dosage form will vary depending upon the host treated and the particular mode of administration.

It is understood, however, that a specific dose level for any particular patient will depend upon a variety of factors including the activity of the specific compound employed, the age, body weight, general health, sex, diet, time of administration, rate of excretion, drug combination, and the severity of the particular disease being treated and form of administration.

The compounds can be administered with other neurotrophic agents such as neurotrophic growth factor (NGF), glial derived growth factor, brain derived growth factor, ciliary neurotrophic factor, and neurotropin-3. The dosage level of other neurotrophic drugs will depend upon the factors previously stated and the neurotrophic effectiveness of the drug combination.

Pharmaceutical Compositions of the Invention

The present invention also relates to a pharmaceutical composition comprising:

(i) a neurotrophically effective amount of the compound of formula I, II, III or IV, and (ii) a pharmaceutically acceptable carrier.

The above discussion relating to the utility and administration of the compounds of the present invention also applies to the pharmaceutical compositions of the present invention.

Methods of Making the Compounds of the Invention

The novel compounds of this invention may be readily prepared by standard techniques of organic chemistry, utilizing the general synthetic pathway depicted below. As described by Scheme I, cyclic amino acids 1 protected by suitable blocking groups P on the amino acid nitrogen may be reacted with thiols RSH to generate thioesters 2. After removal of the protecting group, the free amine 3 may be reacted with various sulfonyl chlorides 4 to provide final products 5 in good to excellent yield.

SCHEME 1

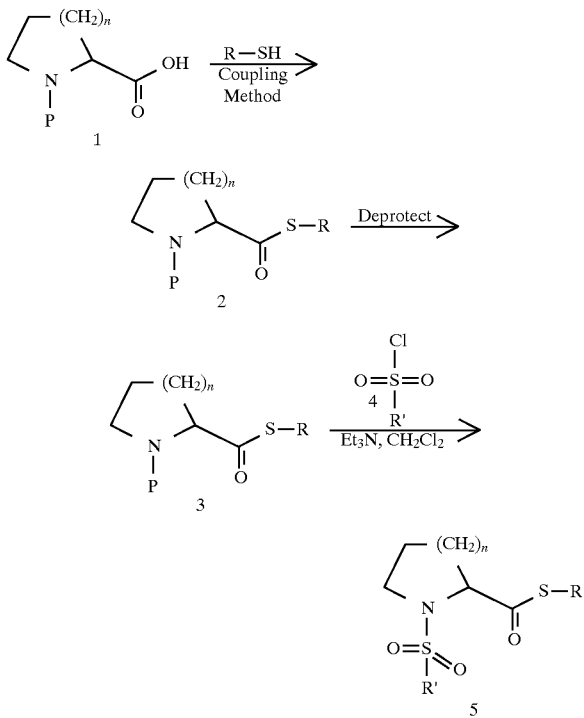

Thiols R-SH may be conveniently prepared from the corresponding readily available alcohols or halides via a two step replacement of halogen by sulfur, as described in Scheme II. Halides may be reacted with thiourea, and the corresponding alkyl thiouronium salts hydrolyzed to provide thiols RSH. If alcohols are used as the starting materials, they may be first converted to the corresponding halides by standard methods.

SCHEME 2

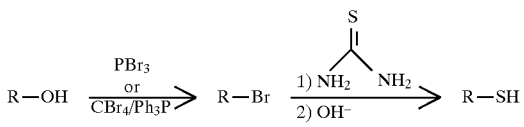

EXAMPLES

The following examples are illustrative of the present invention and are not intended to be limitations thereon. Unless otherwise specified, all percentages are based on 100% by weight of the final compound.

Example 1
Synthesis of 3-(para-Methoxyphenyl)-1-propylmercaptyl (2S)-N-(benzenesulfonyl)pyrrolidine-2-carboxylate(4)
3-(p-Methoxyphenyl)-1-propylbromide To a solution of 3-(p-methoxyphenyl)-1-propanol (16.6 g; 0.1 mol) in 250 mL of tolune, cooled to 0° C., was added dropwise 26 mL of phosphorus tribromide (0.27 mol). Following completion of the addition the reaction was stirred at room temperature for 1 hour, then refluxed for an additional hour. The reaction was cooled and poured onto ice, the layers were separated, and the organic phase washed with saturated sodium bicarbonate (3×) and brine (3×). The crude material obtained upon drying and evaporation of the solvent was chromatographed, eluting with 10%, EtOAc/hexane, to obtain 14 g (61%) of 3-(p-methoxyphenyl)-1-propylbromide.

3-(p-Methoxyphenyl)-1-propylmercaptan

A mixture of 3-(p-methoxyphenyl)-1-propylbromide (14 g; 61 mmol) and thiourea (5.1 g; 67 mmol) in ethanol (150 mL) was refluxed for 48 hours. Evaporation of the solvent provided a clear glassy compound, which was dissolved in 50 mL of water and treated with 100 mL of 40% aqueous sodium hydroxide. After stirring the resulting mixture for two hours, the product was extracted into ether (3×), and the combined organic extracts were washed with sodium bicarbonate and brine, dried, and concentrated. Chromatographic purification of the crude thiol on a silica gel column eluting with 2% either in hexane delivered 10.2 g of 3-(p-methoxyphenyl)-1-propylmercaptan as a clear liquid $^1$H NMR (300 MHz, CDCl$_3$):δ 1.34 (t, 1H); 1.88–1.92 (m,2H); 2.49–2.53 (m,2H); 2.64–2.69 (m, 2H); 3.77 (s, 3H); 6.80–6.84 (m,2H); 7.06–7.24 (m,2H).

3-(p-Methoxyphenyl)-1-mercaptyl N-(tert-butylyoxycarbonyl)pyrrolidine-2-carboxylate A mixture of N-(tert-butylyoxycarbonyl)-(S)-proline (2.0g; 9.29 mmol); 3-(p-methoxyphenyl)-1-propylmercaptan (1.86 g; 10.22 mmol), 1-(3-dimethylaminopropyl)-3-ethylcarbodiimide hydrochloride (1.96 g; 10.22 mmol) and 4-dimethylaminopyridine (catalytic) in dry methylene chloride (50 mL) was stirred overnight. The reaction mixture was diluted with methylene chloride (50 mL) and water 100 (mL), and the layers were separated. The organic phase was washed with water (3×100 mL), dried over magnesium sulfate, and concentrated to provide 3.05 g of the product as a thick oil, $^1$H NMR (300 MHz, CDCl$_3$) :δ 1.15 (s, 9H); 1.84–2.31 (m,6H); 2.61 (m,2H); 2.83 (m, 2H); 3.51 (m, 2H); 3.75 (s,3H); 6.79 (d,2H, J=8.04); 7.05 (m,2H).

3-(p-Methoxyphenyl)-1-mercaptyl pyrrolidine-2-carboxylate

A solution of 3-(p-methoxyphenyl)-mercaptyl N-(tert-butylyoxycarbonyl)pyrrolidine-2-carboxylate (3.0 g; 8.94 mmol) in methylene chloride (60 mL) and trifluoroacetic acid (6 mL) was stirred at room temperature for three hours. Saturated potassium carbonate was added until the pH was basic, and the reaction mixture was extracted with methylene chloride (3×). The combined organic extracts were dried and concentrated to yield 1.73 g(69%) of the free amine as a thick oil, $^1$H NMR (300 MHz, CDCl$_3$):δ 1.80–2.23 (m, 6H); 2.62 (m,2H); 2.81 (m, 2H); 3.01 (m, 2H); 3.75 (s,3H); 3.89(m,1H); 6.81 (m,2H); 7.06 (m,2H).

3-(para-Methoxyphenyl)-1-propylmercaptyl (2S)-N-(benzenesulfonyl)pyrrolidine-2-carboxylate A solution of 3-(p-methoxyphenyl)-1-mercaptyl pyrrolidine-2-carboxylate (567 mg; 2.03 mmol) and benzenesulfonyl chloride (358 mg; 2.03 mmol) in methylene chloride (5 mL) was treated with diisopropylethylamine (290 mg; 2.23 mmol) and stirred overnight at room temperature. The reaction mixture was filtered to remove solids and applied directly to a silica gel column, eluting with 25% ethyl acetate in hexane, to obtain 540 mg of compound 4 (Table I) as a clear oil, $^1$H NMR (300 MHz, CDCl$_3$):δ 1.65–1.89 (m,6H); 2.61 (t, 2H, J=7.3); 2.87 (t,2H,J=7.6); 3.26(m,1H); 3.54 (m,1H); 3.76 (s,3H); 4.34 (dd,1H,J=2.7, 8.6); 6.79 (d,2H, J=8.7); 7.06(d, 2H, J=8.6); 7.9–7.594 (m,3H); 7.86(dd, 2H, J=1.5,6.8).

Example 2
Synthesis of 3-(para-Methoxyphenyl)-1-propylmercaptyl (2S)-N-(α-toluenesulfonyl)pyrrolidine-2-carboxylate (5)

A solution of 3-(p-Methoxyphenyl)-1-mercaptyl pyrrolidine-2-carboxylate (645 mg; 2.30 mmol) and α-toluenesulfonyl chloride (440 mg; 2.30 mmol) in methylene chloride (5 mL) was treated with diisopropylethylamine (330 mg; 2.53 mmol) and stirred overnight at room temperature. Purification as described for Example 1 provided the compound of Example 2 (Compound 5, Table I) as a clear oil, $^1$H NMR (300 MHz, CDCl$_3$): δ 1.65–2.25 (m,8H) ; 2.65 (t, 2H); 2.89–2.96 (m,2H); 3.55–3.73 (m,2H); 3.80 (s,3H); 4.32 (s,2H); 4.70–4.81 (m,1H); 6.83 (d,2H); 7.09 (d,2H); 7.14 (m,3H); 7.26 (m,2H).

Example 3
Synthesis of 3-(para-Methoxyphenyl)-1-propylmercaptyl (2S)-N-(α-toluenesulfonyl)pyrrolidine-2-carboxylate (6)

A solution of 3-(p-Methoxyphenyl)-1-mercaptyl pyrrolidine-2-carboxylate (567 mg; 2.30 mmol) and p-toluenesulfonyl chloride (425 mg; 2.23 mmol) in methylene chloride (5 mL) was stirred overnight at room temperature. Purification as described for Example 1 provided the compound of Example 3 (Compound 6, Table I) as a clear oil, $^1$H NMR (300 MHz, CDCl$_3$):δ 1.67–1.94 (m,6H); 2.40 (s,3H); 2.61 (t,2H,J=7.3); 2.84 (m,2H,J=7.2); 3.22 (m,1H); 3.52 (m,1H); 3.76 (s,3H); 4.32 (dd,1H,J-2.9,8.5); 6.79 (d,2H,J=6.5); 7.07(d,2H,J=6.5); 7.29 (d,2H,J=6.5); 7.74 (d,2H,J=6.5).

Example 4
Synthesis of 1,5-Diphenyl-3-pentylmercaptyl N-(para-toluenesulfonyl)pipecolate (18)
3-Phenyl-1-propanal Oxalyl chloride (2.90 g; 2.29 mmol) in methylene chloride (50 mL), cooled to −78° C., was treated with dimethylsulfoxide (3.4 mL) in 10 mL of methylene chloride. After stirring for 5 min, 3-phenyl-1-propanol (2.72 g; 20 mmol) in 20 mL of methylene chloride was added, and the resulting mixture was stirred at −78° C. for 15 min, treated with 14 mL of triethylamine, stirred an additional 15 min, and poured into 100 mL of water. The layers were separated, the organic phase was dried and concentrated, and the crude residue was purified on a silica gel column, eluting with 10% ethyl acetate in hexane, to obtain 1.27 g (479) of the aldehyde as a clear oil, $^1$H NMR (300 MHz, CDCl$_3$): δ 2.80(m,2H); 2.98(m,2H); 7.27(m,5H); 9.81(2,1H).

1.5-Diphenyl-3-pentanol

A solution of 2-(bromoethyl)benzene (1.73 g; 9.33 mmol) in diethylether (10 mL) was added to a stirred slurry of magnesium turnings (250 mg; 10.18 mmol) in 5 mL of ether. The reaction was initiated with a heat gun, and after the addition was complete the mixture was heated on an oil bath for 30 min. 3-Phenyl-1-propanal (1.25 g; 9.33 mmol) was added in 10 mL of ether, and reflux was continued for 1 hr. The reaction was cooled and quenched with saturated ammonium chloride, extracted into 2× ethyl acetate, and the combined organic portions were dried and concentrated. Chromatographic purification on a silica gel column (10% ethyl acetate in hexane) delivered 1.42 g(63%) of the dipehnyl alcohol, $^1$H NMR (300 MHz, CDCl$_3$): δ 1.84(m, 4H); 2.61–2.76(m,4H); 3.65(m,1H); 7.19–7.29(m,10H).

1,5-Diphenyl-3-bromopentane

To a solution of 1,5-diphenyl-3-pentanol (1.20 g(5 mmol) and carbon tetrabromide (1.67 g(5 mmol) in methylene chloride (20 mL) was added triphenylphosphine (1.31 g; 5 mmol) portionwise, at 0° C. After stirring at room temperature for 18 hours, the mixture was concentrated, triturarated with ether, and the solids removed by filtration. The filtrate was passed through a plug of silica gel, eluting with hexane:methylene chloride, 10:1, to give 1.35 g (90%) of the bromide as an oil which was used without further purification. $^1$H NMR (300 MHz, CDCl$_3$) δ 2.11–2.18(m,4H); 2.73 (m,2H); 2.86 (m,2H); 3.95 (m,1H); 7.16–7.30(m,10H).

1,5-Diphenyl-3-pentylmercaptan

Using the procedure described in Example 1 for the conversion of bromides to thiols, 1,5-diphenyl-3-bromopentane was converted to 1,5-diphenyl-3-pentylmercaptan in 35% overall yield, $^1$H NMR (300 MHz, CDCl$_3$) : δ 1.79(m,2H); 1.98(m,2H); 2.71(m,3H); 2.80(m, 2H); 7.16–7.28(m,10H).

1,5-Diphenyl-3-pentylmercaptyl N-(tert-butylyoxycarbonyl)pyrrolidine-2-carboxylate A mixture of N-(tert-butylyoxycarbonyl)-(S)-pipecolic acid (0.11 g; 9.29 mmol), 1,5-diphenyl-3-pentylmercaptan (2.58 g; 10.22 mmol), 1-(3-dimethylaminopropyl)-3-ethylcarbodiimide hydrochloride (1.96 g; 10.22 mmol) and 4-dimethylaminopyridine (catalytic) in dry methylene chloride 950 mL) was stirred overnight the reaction mixture was diluted with methylene chloride (50 mL) and water (100 mL), and the layers were separated. The organic phase was washed with water (3×100 mL), dried over magnesium sulfate, and concentrated to provide 870 mg (20%) of the product as a thick oil, which was used without further purification.

1,5-Diphenyl-3-pentylmercaptyl pyrrolidine-2-carboxylate

A solution of 1,5-diphenyl-3-pentylmercaptyl N-(tert-butylyoxycarbonyl)-pyrrolidine-2-carboxylate (850 mg; 1.8 mmol) in methylene chloride (10 mL) and trifluoroacetic acid (1 mL) was stirred at room temperature for three hours. Saturated potassium carbonate was added until the pH was basic, and the reaction mixture was extracted with methylene chloride. The combined organic extracts were dried and concentrated to yield 480 mg (72%) of the free amine as a thick oil, which was used without further purification.

1,5-Diphenyl-3-pentylmercaptyl N-(para-toluenesulfonyl) pipecolate (19)

1,5-Diphenyl-3-pentylmercaptyl N-(para-toluenesulfonyl)pipecolate(18) was prepared from 1,5-diphenyl-3-pentylmercaptyl pyrrolidine-2-carboxylate and para-toluenesulfonyl chloride as described for Example 3, in 65% yield, $^1$H NMR (CDCl$_3$, 300 MHz): δ 0.80(m,4H); 1.23–1.97 (m,5H); 2.15 (d, 1H); 2.61–2.69 (m,4H); 3.23 (m,1H); 3.44(dm, 1H); 4.27 (s,2H); 4.53(d,1H, J-4.5);5.06 (m,1H); 7.16–7.34(m,15H).

As discussed above, the compounds of the present invention have an affinity for the FK506 binding protein, particularly FKBP12. The inhibition of the prolyl peptidyl cis-trans isomerase activity of FKBP may be measured as an indicator of this affinity.

Ki Test Procedure

Inhibition of the peptidyl-prolyl isomnerase (rotamase) activity of the inventive compounds can he evaluated by known methods described in the literature (Harding, et al., *Nature*, 1989, 341:758–760; Holt et al. *J. Am. Chem. Soc.*, 115:9923–9938). These values are obtained as apparent Ki's and are presented in Table II. The cis-trans isomerization of an alanine-proline bond in a model substrate, N-succinyl-Ala-Ala-Pro-Phe-p-nitroanilide, is monitored spectrophotometrically in a chymotrypsin-coupled assay, which releases para-nitroanilide from the trans form of the substrate. The inhibition of this reaction caused by the addition of different concentrations of inhibitor is determined, and the data is analyzed as a change in first-order rate constant as a function of inhibitor concentration to yield the apparent Ki values.

In a plastic cuvette are added 950 mL of ice cold assay buffer (25 mM HEPES, pH 7.8, 100 mM NaCl), 10 mL of FKBP (2.5 mM in 10 mM Tris-Cl pH 7.5, 100 mM NaCl, 1 mM dithiothreitol), 25 mL of chymotrypsin (50 mg/ml in 1 mM HCl) and 10 mL of test compound at various concentrations in dimethyl sulfoxide. The reaction is initiated by the addition of 5 mL of substrate (succinyl-Ala-Phe-Pro-Phe-para-nitroanilide, 5 mg/mL in 2.35 mM LiCl in trifluoroethanol).

The absorbance at 390 nm versus time is monitored for 90 seconds using a spectrophotometer and the rate constants are determined from the absorbance versus time data files.

The data for these experiments for representative compounds are presented in Table II under the column "Ki".

The neurotrophic effects of the compounds of the present invention can be demonstrated in cellular biological experiments in vitro, as described below.

Chick Dorsal Root Ganglion Cultures and Neurite Outgrowth

Dorsal root ganglia were dissected from chick embryos of ten day gestation. Whole ganglion explants were cultured on thin layer Matrigel-coated 12 well plates with Liebovitz L15 plus high glucose media supplemented with 2 mM glutamine and 10% fetal calf serum, and also containing 10 $\mu$M cytosine $\beta$-D arabinofuranoside (Ara C) at 37° C. in an environment containing 5% $CO_2$. Twenty-four hours later, the DRGs were treated with various immunophilin ligands. Forty-eight hours after drug treatment, the ganglia were visualized under phase contrast or Hoffman Modulation contrast with a Zeiss Axiovert inverted microscope. Photomicrographs of the explants were made, and neurite outgrowth was quantitated. Neurites longer than the DRG diameter were counted as positive, with total number of neurites quantitated per each experimental condition. Three to four DRGs are cultured per well, and each treatment was performed in duplicate.

The data for these experiments for representative compounds are presented in Table II under the column "$ED_{50}$".

TABLE II

In Vitro Test Results

| Ex. No. | Ki,nM[a] | ED50,nM[a] |
|---|---|---|
| 1 | +++ | ++++ |
| 2 | ++ | +++ |
| 3 | ++ | +++ |
| 4 | ++ | ++ |
| 5 | ++ | +++ |
| 6 | + | ++ |
| 7 | ++ | +++ |
| 8 | +++ | ++++ |
| 9 | +++ | ++++ |
| 10 | +++ | +++ |
| 11 | ++ | +++ |
| 12 | +++ | +++ |
| 13 | +++ | ++++ |
| 14 | +++ | +++ |
| 15 | +++ | ++++ |
| 16 | ++ | ++ | a. Relative potencies of compounds are ranked according to the following scale: ++++ denotes Ki or ED50<1 nM; +++ denotes Ki or ED50 of 1–50 nM; ++ denotes Ki or ED 50 of 51–200 nM; + denotes Ki or ED of 201–500 nM.

MPTP Model of Parkinson's Disease

The remarkable neurotrophic and neuroregenerative effects of the present inventive compounds can be further demonstrated in an animal model of neurodegenerative disease. MPTP lesioning of dopaminergic neurons in mice is used as an animal model of Parkinson's Disease. Four week old male CD1 white mice are dosed i.p. with 30 mg/kg of MPTP for 5 days. Test compounds (4 mg/kg), or vehicle, are administered s.c. along with the MPTP for 5 days, as well as for an additional 5 days following cessation of MPTP treatment. At 18 days following MPTP treatment, the animals are sacrificed and the striata dissected and perfusion-fixed. Immunostaining is performed on saggital and coronal brain sections using anti-tyrosine hydroxylase 1 g to quantitate survival and recovery of dopaminergic neurons. In animals treated with MPTP and vehicle, a substantial loss of functional dopaminergic terminals is observed as compared to non-lesioned animals. Lesioned animals receiving test compounds show a significant recovery of TH-stained dopaminergic neurons. This model presents quantitation for the recovery of TH-positive dopaminergic neurons in the striatum of animals receiving the compounds of the present invention. Data for representative control and lesioned animals not receiving the test drugs is also presented against the data from the animals receiving the compounds of the present invention.

The invention being thus described, it will be obvious that the same may be varied in many ways. Such variations are not to be regarded as a departure from the spirit and scope of the invention and all such modification are intended to be included within the scope of the following claims.

What is claimed is:

1. A compound of formula I:

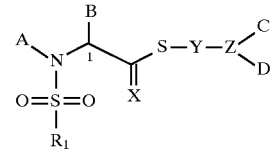

or a pharmaceutically acceptable salt thereof, wherein:

A and B are taken together, with the nitrogen and carbon atoms to which they are respectfully attached, to form a pyrrolidine or piperidine ring;

X is either O or S, with the proviso that when A and B taken together with the nitrogen and carbon atoms to which they are attached form a piperidine ring, then X is not S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, or ($C_1$–$C_4$) bridging alkyl wherein a bridge is formed between the nitrogen and a carbon atom of said alkyl or alkenyl chain containing said heteroatom to form a pyrrolidine, piperidine, furanyl, or thienyl ring;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

C and D are independently:
hydrogen, or Ar, or $C_1-C_6$ straight or branched chain alkyl or alkenyl, which is optionally substituted in one or more positions with $C_3-C_8$ cycloalkyl, $C_5-C_7$ cycloalkenyl, hydroxyl, carbonyl oxygen, or with Ar, where said alkyl, alkenyl, cycloalkyl or cycloalkenyl groups is optionally substituted with $C_1-C_4$ alkyl, $C_1-C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

wherein Ar is a pyrrolidine, piperidine, furanyl, or thienyl ring, wherein the ring is either unsubstituted or substituted in one to three positions with halo, hydroxyl, nitro, trifluoromethyl, $C_1-C_6$ straight or branched chain alkyl or alkenyl, $C_1-C_4$ alkoxy, $C_1-C_4$ alkenyloxy, phenoxy, benzyloxy, amino, or a combination thereof;

$R_1$ is selected from the group consisting of Ar, or $C_3-C_8$ cycloalkyl, or $C_1-C_6$ straight or branched chain alkyl or alkenyl, or $C_1-C_6$ straight or branched chain alkyl or alkenyl which is substituted in one or more positions with Ar or $C_3-C_8$ cycloalkyl.

2. The compound of claim 1, wherein the compound is has an affinity for FKBP-type immunophilins.

3. The compound of claim 2, wherein the FKBP-type immunophilins are FKBP12.

4. The compound of claim 1, wherein the compound inhibits rotamase enzyme activity.

5. The compound of claim 1, wherein the compound is selected from the group consisting of:
3-(para-Methoxyphenyl)-1-propylmercaptyl (2S)-N-(benzensulfonyl)pyrrolidine-2-carboxylate;
3-(para-Methoxyphenyl)-1-propylmercaptyl (2S)-N-(α-toluenesulfonyl)pyrrolidine-2-carboxylate;
3-(para-Methoxyphenyl)-1-propylmercaptyl (2S)-N-(α-toluenesulfonyl)pyrrolidine-2-carboxylate; and
1,5-Diphenyl-3-pentylmercaptyl N-(para-toluenesulfonyl)pipecolate.

6. A pharmaceutical composition comprising a neurotrophically effective amount of the compound of claim 1 and a pharmaceutically acceptable carrier.

7. A method of effecting a neuronal activity in an animal, the neuronal activity selected from the group consisting of stimulation of damaged neurons, promotion of neuronal regeneration, and treatment of a neurological disorder, wherein the neurological disorder is selected from the group consisting of peripheral neuropathy caused by physical injury or disease state, physical damage to the brain, physical damage to the spinal cord, stroke associated with brain damage, and neurological disorders related to neurodegeneration, and wherein the neurological disorders related to neurodegeneration are selected from the group consisting of Alzheimer's Disease, Parkinson's Disease, and amyotrophic lateral sclerosis, the method comprising:
administering to the animal a neurotrophically effective amount of the compound of claim 1.

8. A compound of formula II:

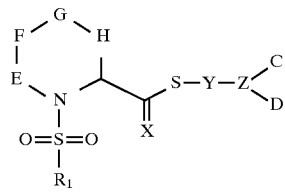

or a pharmaceutically acceptable salt thereof, wherein:
E, F, G and H are independently $CH_2$;
X is either O or S, with the proviso that when A and B taken together with the nitrogen and carbon atoms to which they are attached form a piperidine ring, then X is not S;
Y is a direct bond to Z, or a $C_1-C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

Z is a direct bond, or a $C_1-C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

C and D are independently:
hydrogen, or Ar, or $C_1-C_6$ straight or branched chain alkyl or alkenyl, which is optionally substituted in one or more positions with $C_3-C_8$ cycloalkyl, $C_5-C_7$ cycloalkenyl, hydroxyl, carbonyl oxygen, or with Ar, where said alkyl, alkenyl, cycloalkyl or cycloalkenyl groups is optionally substituted with $C_1-C_4$ alkyl, $C_1-C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

wherein Ar is a pyrrolidine, piperidine, furanyl, or thienyl ring, wherein the ring is either unsubstituted or substituted in one to three positions with halo, hydroxyl, nitro, trifluoromethyl, $C_1-C_6$ straight or branched chain alkyl or alkenyl, $C_1-C_4$ alkoxy, $C_1-C_4$ alkenyloxy, phenoxy, benzyloxy, amino, or a combination thereof; and $R_1$ is selected from the group consisting of Ar, or $C_3-C_8$ cycloalkyl, or $C_1-C_6$ straight or branched chain alkyl or alkenyl, or $C_1-C_6$ straight or branched chain alkyl or alkenyl which is substituted in one or more positions with Ar or $C_3-C_8$ cycloalkyl.

9. The compound of claim 8, wherein the compound has an affinity for FKBP-type immunophilins.

10. The compound of claim 8, wherein the FKBP-type immunophilins are FKBP12.

11. The compound of claim 8, wherein the compound inhibits rotamase enzyme activity.

12. A pharmaceutical composition comprising a neurotrophically effective amount of the compound of claim 8 and a pharmaceutically acceptable carrier.

13. A method of effecting a neuronal activity in an animal, the neuronal activity selected from the group consisting of stimulation of damaged neurons, promotion of neuronal regeneration, and treatment of a neurological disorder, wherein the neurological disorder is selected from the group consisting of peripheral neuropathy caused by physical injury or disease state, physical damage to the brain, physical damage to the spinal cord, stroke associated with brain damage, and neurological disorders related to neurodegeneration, and wherein the neurological disorders related to neurodegeneration are selected from the group consisting of Alzheimer's Disease, Parkinson's Disease, and amyotrophic lateral sclerosis, the method comprising:

administering to the animal a neurotrophically effective amount of the compound of claim 8.

14. A compound of formula III:

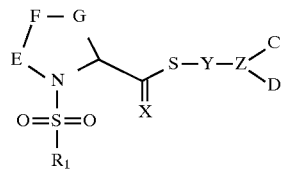

III or a pharmaceutically acceptable salt thereof, wherein:

E, F and G are independently $CH_2$;

X is either O or S;

Y is a direct bond to Z, or a $C_1-C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

Z is a direct bond, or a $C_1-C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

C and D are independently:

hydrogen, or Ar, or $C_1-C_6$ straight or branched chain alkyl or alkenyl, which is optionally substituted in one or more positions with $C_3-C_8$ cycloalkyl, $C_5-C_7$ cycloalkenyl, hydroxyl, carbonyl oxygen, or with Ar, where said alkyl, alkenyl, cycloalkyl or cycloalkenyl groups is optionally substituted with $C_1-C_4$ alkyl, $C_1-C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, $(C_1-C_4)$-straight or branched chain alkyl, $(C_3-C_4)$-straight or branched chain alkenyl or alkynyl, or $(C_1-C_4)$ bridging alkyl wherein a bridge is formed between the nitrogen and a carbon atom of said alkyl or alkenyl chain containing said heteroatom to form a pyrrolidine, piperidine, furanyl, or thienyl ring;

wherein Ar is a pyrrolidine, piperidine, furanyl, or thienyl ring, wherein the ring is either unsubstituted or substituted in one to three positions with halo, hydroxyl, nitro, trifluoromethyl, $C_1-C_6$ straight or branched chain alkyl or alkenyl, $C_1-C_4$ alkoxy, $C_1-C_4$ alkenyloxy, phenoxy, benzyloxy, amino, or a combination thereof; and $R_1$ is selected from the group consisting of Ar, or $C_3-C_8$ cycloalkyl, or $C_1-C_6$ straight or branched chain alkyl or alkenyl, or $C_1-C_6$ straight or branched chain alkyl or alkenyl which is substituted in one or more positions with Ar or $C_3-C_8$ cycloalkyl.

15. The compound of claim 14, wherein the compound has an affinity for FKBP-type immunophilins.

16. The compound of claim 14, wherein the FKBP-type immunophilins are FKBP12.

17. The compound of claim 14, wherein the compound inhibits rotamase enzyme activity.

18. A pharmaceutical composition comprising a neurotrophically effective amount of the compound of claim 14 and a pharmaceutically acceptable carrier.

19. The method of effecting a neuronal activity in an animal, the neuronal activity selected from the group consisting of stimulation of damaged neurons, promotion of neuronal regeneration, and treatment of a neurological disorder, wherein the neurological disorder is selected from the group consisting of peripheral neuropathy caused by physical injury or disease state, physical damage to the brain, physical damage to the spinal cord, stroke associated with brain damage, and neurological disorders related to neurodegeneration, and wherein the neurological disorders related to neurodegeneration are selected from the group consisting of Alzheimer's Disease, Parkinson's Disease, and amyotrophic lateral sclerosis, the method, comprising:

administering to the animal a neurotrophically effective amount of the compound of claim 14.

20. A compound of formula IV:

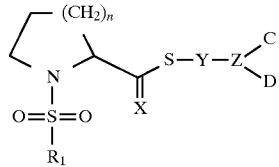

or a pharmaceutically acceptable salt thereof, wherein:

n is 1 or 2 forming a pyrrolidine or piperidine ring;

X is either O or S, with the proviso that when A and B taken together with the nitrogen and carbon atoms to which they are attached form a piperidine ring, then X is not S;

Y is a direct bond to Z, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, or ($C_1$–$C_4$) bridging alkyl wherein a bridge is formed between the nitrogen and a carbon atom of said alkyl or alkenyl chain containing said heteroatom to form a pyrrolidine, piperidine, furanyl, or thienyl ring;

Z is a direct bond, or a $C_1$–$C_6$ straight or branched chain alkyl or alkenyl, wherein any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, or ($C_1$–$C_4$) bridging alkyl wherein a bridge is formed between the nitrogen and a carbon atom of said alkyl or alkenyl chain containing said heteroatom to form a pyrrolidine, piperidine, furanyl, or thienyl ring;

C and D are independently:

hydrogen, or Ar, or $C_1$–$C_6$ straight or branched chain alkyl or alkenyl, which is optionally substituted in one or more positions with $C_3$–$C_8$ cycloalkyl, $C_5$–$C_7$ cycloalkenyl, hydroxyl, carbonyl oxygen, or with Ar, where said alkyl, alkenyl, cycloalkyl or cycloalkenyl groups is optionally substituted with $C_1$–$C_4$ alkyl, $C_1$–$C_4$ alkenyl, or hydroxy, where any of the carbon atoms of said alkyl or alkenyl is optionally substituted in one or more positions with oxygen to form a carbonyl, or wherein any of the carbon atoms of said alkyl or alkenyl is optionally replaced with O, NH, $NR_2$, S, SO, or $SO_2$, where $R_2$ is selected from the group consisting of hydrogen, ($C_1$–$C_4$)-straight or branched chain alkyl, ($C_3$–$C_4$)-straight or branched chain alkenyl or alkynyl, or ($C_1$–$C_4$) bridging alkyl wherein a bridge is formed between the nitrogen and a carbon atom of said alkyl or alkenyl chain containing said heteroatom to form a pyrrolidine, piperidine, furanyl, or thienyl ring;

wherein Ar is a pyrrolidine, piperidine, furanyl, or thienyl ring, wherein the ring is either unsubstituted or substituted in one to three positions with halo, hydroxyl, nitro, trifluoromethyl, $C_1$–$C_6$ straight or branched chain alkyl or alkenyl, $C_1$–$C_4$ alkoxy, $C_1$–$C_4$ alkenyloxy, phenoxy, benzyloxy, amino, or a combination thereof; and $R_1$ is selected from the group consisting of Ar, or $C_3$–$C_8$ cycloalkyl, or $C_1$–$C_6$ straight or branched chain alkyl or alkenyl, or $C_1$–$C_6$ straight or branched chain alkyl or alkenyl which is substituted in one or more positions with Ar or $C_3$–$C_8$ cycloalkyl.

21. The compound of claim 20, wherein the compound has an affinity for FKBP-type immunophilins.

22. The compound of claim 20, wherein the FKBP-type immunophilins are FKBP12.

23. The compound of claim 20, wherein the compound inhibits rotamase enzyme activity.

24. A pharmaceutical composition comprising a neurotrophically effective amount of the compound of claim 20 and a pharmaceutically acceptable carrier.

25. A method of effecting a neuronal activity in an animal, the neuronal activity selected from the group consisting of stimulation of damaged neurons, promotion of neuronal regeneration, and treatment of a neurological disorder, wherein the neurological disorder is selected from the group consisting of peripheral neuropathy caused by physical injury or disease state, physical damage to the brain, physical damage to the spinal cord, stroke associated with brain damage, and neurological disorders related to neurodegeneration, and wherein the neurological disorders related to neurodegeneration are selected from the group consisting of Alzheimer's Disease, Parkinson's Disease, and amyotrophic lateral sclerosis, the method, comprising:

administering to the animal a neurotrophically effective amount of the compound of claim 20.

26. A method of treating neurological disorders relating to neurodegeneration selected from the group consisting of Parkinson's disease, Alzheimer's disease, and amyotrophic lateral sclerosis, comprising administering to an animal a neurotrophically effective amount of the compound of claim 1.

27. A method of treating neurological disorders relating to neurodegeneration selected from the group consisting of Parkinson's disease, Alzheimer's disease, and amyotrophic lateral sclerosis, comprising administering to an animal a neurotrophically effective amount of the compound of claim 8.

28. A method of treating neurological disorders relating to neurodegeneration selected from the group consisting of Parkinson's disease, Alzheimer's disease, and amyotrophic lateral sclerosis, comprising administering to the animal a neurotrophically effective amount of the compound of claim 14.

29. A method of treating neurological disorders caused by neurodegenerative diseases, consisting essentially of Parkinson's disease, Alzheimer's disease, and amyotrophic lateral sclerosis, comprising administering to the animal a neurotrophically effective amount of the compound of claim 20.

30. A method of treating neurological disorders caused by physical injury, consisting essentially of peripheral nerve damage, and physical damage to the central nervous system, comprising administering to the animal a neurotrophically effective amount of the compound of claim 1.

31. A method of treating neurological disorders caused by physical injury, consisting essentially of peripheral nerve damage, and physical damage to the central nervous system, comprising administering to the animal a neurotrophically effective amount of the compound of claim 8.

32. A method of treating neurological disorders caused by physical injury, consisting essentially of peripheral nerve damage, and physical damage to the central nervous system, comprising administering to the animal a neurotrophically effective amount of the compound of claim 14.

33. A method of treating neurological disorders caused by physical injury, consisting essentially of peripheral nerve damage, and physical damage to the central nervous system, comprising administering to the animal a neurotrophically effective amount of the compound of claim 20.

* * * * *

UNITED STATES PATENT AND TRADEMARK OFFICE
CERTIFICATE OF CORRECTION

PATENT NO. : 5,874,449
DATED : February 23, 1999
INVENTOR(S) : Hamilton et al.

It is certified that error appears in the above-identified patent and that said Letters Patent is hereby corrected as shown below:

Column 6, line 27, replace "$(C_1-C_4,)$" with --$(C_1-C_4)$--

Column 7, line 41, replace "$(C_1-C_4,)$" with --$(C_1-C_4)$--

Column 15, line 47, replace "(479)" with --(47%)--

Column 16, line 24, replace "overnight the reaction"

with --overnight. The reaction--

Signed and Sealed this

Twenty-ninth Day of February, 2000

Attest:

Attesting Officer

Q. TODD DICKINSON

Commissioner of Patents and Trademarks

UNITED STATES PATENT AND TRADEMARK OFFICE
CERTIFICATE OF CORRECTION

PATENT NO.    : 5,874,449  
DATED         : February 23, 1999  
INVENTOR(S)   : Gregory S. Hamilton et al.

It is certified that error appears in the above-identified patent and that said Letters Patent is hereby corrected as shown below:

Column 19,  
Line 38, after "combination thereof;", please insert -- and --.  
Line 44, after "wherein the compound" and before "has", please remove -- is --.

Column 22,  
Line 55, before "method of effecting", please replace "The" with -- A --.

Signed and Sealed this

Thirteenth Day of May, 2003

JAMES E. ROGAN  
*Director of the United States Patent and Trademark Office*